(12) United States Patent
Sundhar

(10) Patent No.: US 7,178,523 B2
(45) Date of Patent: Feb. 20, 2007

(54) WATER AND OXYGEN BOTTLE

(75) Inventor: Shaam P Sundhar, Princeton, NJ (US)

(73) Assignee: Beverage Creations, LLC, Saint Paul, MN (US)

( * ) Notice: Subject to any disclaimer, the term of this patent is extended or adjusted under 35 U.S.C. 154(b) by 0 days.

(21) Appl. No.: 11/161,251

(22) Filed: Jul. 28, 2005

(65) Prior Publication Data

US 2006/0174868 A1    Aug. 10, 2006

Related U.S. Application Data

(60) Provisional application No. 60/593,676, filed on Feb. 4, 2005.

(51) Int. Cl.
   *A62B 9/02*   (2006.01)
   *B65D 1/04*   (2006.01)
   *B65D 1/24*   (2006.01)
   *B67D 5/56*   (2006.01)

(52) U.S. Cl. ................... 128/205.24; 215/6; 222/129; 220/506

(58) Field of Classification Search ........... 128/205.24; 141/10, 19, 37, 67–68, 114, 329, 330, 230–247, 141/313–317, 346–382; 222/175, 207, 383, 222/464, 129, 192; 150/55; 220/375, 85 B, 220/66, 403, 503, 506, 553, 581, 585; 206/524.8; 224/148.1–148.7; 215/6, 10, 380

See application file for complete search history.

(56) References Cited

U.S. PATENT DOCUMENTS 3,654,926 A * 4/1972 Rietman .................. 604/416
6,000,395 A * 12/1999 Brown ................. 128/202.19
6,708,692 B2 * 3/2004 Lee et al. .............. 128/205.24

* cited by examiner

*Primary Examiner*—Henry Bennett
*Assistant Examiner*—Shumaya B. Ali
(74) *Attorney, Agent, or Firm*—Patwrite LLC; Mark David Torche

(57) ABSTRACT

A bottle contains at least one oxygen chamber allowing a user to breathe pure oxygen by placing their mouth and nose in a facemask contoured to fit the users face. The bottle also holds water so the user can drink clean pure water as well. The oxygen is pressurized allowing more oxygen to be stored in the chambers and to aid the user in getting the oxygen into his or her lungs. The present invention allows a user to drink water and breathe pure oxygen in a safe and convenient manner.

12 Claims, 5 Drawing Sheets

WATER AND OXYGEN BOTTLE

RELATED APPLICATION

This application claims priority and herein incorporates by reference U.S. provisional patent application No. 60/593,676 Feb. 4, 2005.

BACKGROUND OF THE INVENTION

In the past few years bottled water has become common place. The public has shown that it is willing to purchase water for the convenience and purity of the bottled water. Bottled water is perceived to be relatively free of contaminants and can be placed in coolers, refrigerators, etc. and allow consumers to drink cold clean water almost everywhere without relying on the often dirty warm drinking fountains of the past. This seems to represent a shift in the public's attitude towards purchasing something that has traditionally been thought of as "free."

Additionally, because of pollution, people living in big cities such as Tokyo and San Francisco, some people are breathing pure oxygen in "oxygen bars" where consumers typically inhale oxygen often mixed with a scent for a per minute fee. Users claim that they feel refreshed and invigorated after inhaling the oxygen. Because of the systems used to produce the oxygen can often produce contaminants and the addition of some scents can introduce dangerous bacterium into the lungs of a user, there have been some serious health concerns raised associated with the use of such oxygen bars. Also, in order to benefit from breathing the oxygen, the consumer must visit the bar. There is a need for safe, pure and convenient access to pure oxygen without the dangers or inconvenience associated with visiting an oxygen bar. Of course it is possible to obtain breathable oxygen with a doctor's prescription, this is both impractical for the majority of consumers who just want to benefit from conveniently being able to breath pure oxygen at their pleasure without the bulk of conventional breathable oxygen cylinders. Additionally, doctors will only give a prescription for oxygen to patients who need them for diseases such as emphysema, etc. This does not help those who want to breathe pure oxygen for personal reasons.

There is a need for a clean, inexpensive and safe way to dispense water and oxygen to the general public in order to meet a need for clean water and air.

Other features and advantages of the instant invention will become apparent from the following description of the invention which refers to the accompanying drawings.

DETAILED DECRIPTION OF THE INVENTION

Figure 1:
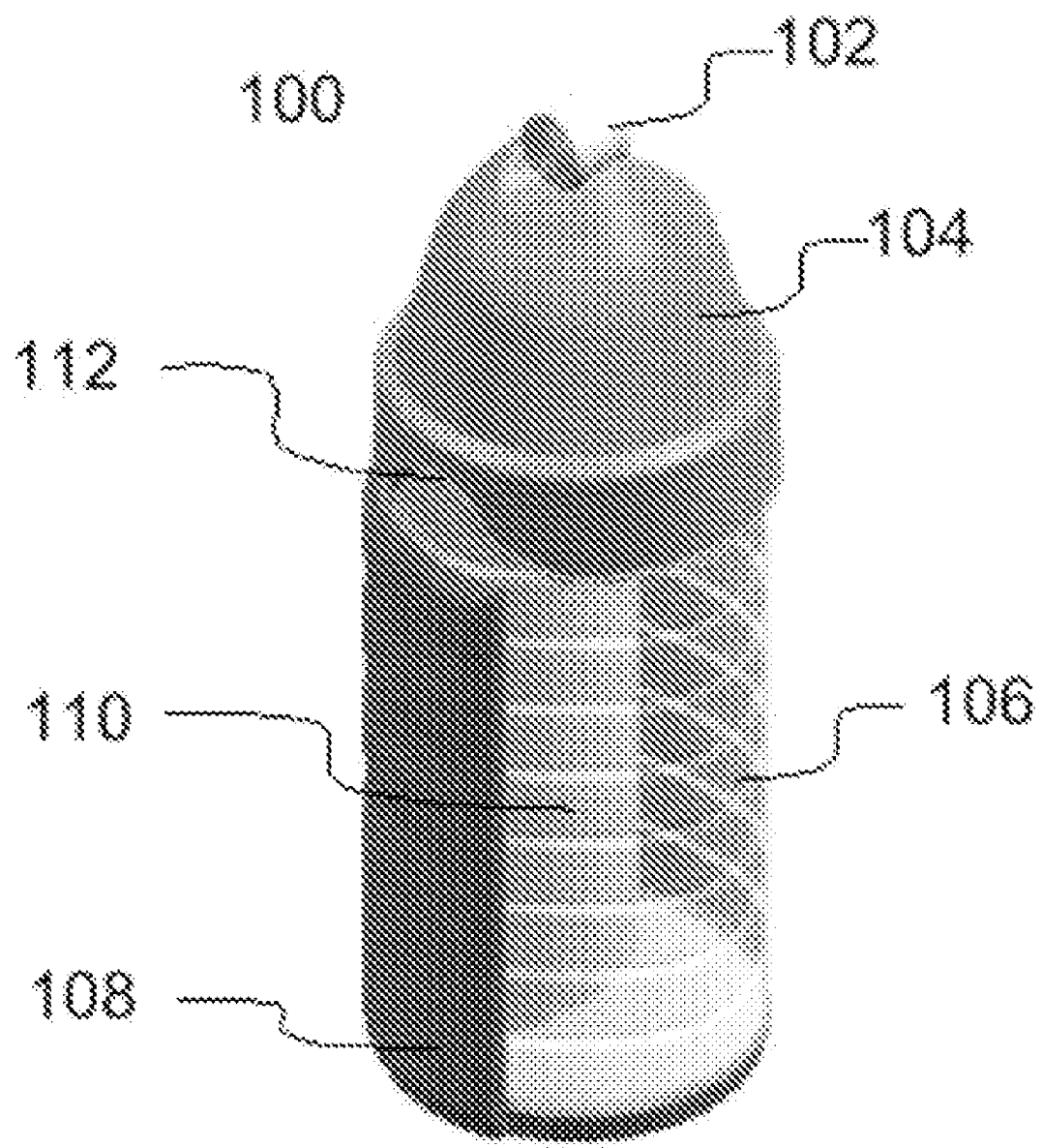
FIG. 1 shows a perspective view of an embodiment of the invention.
Figure 2:
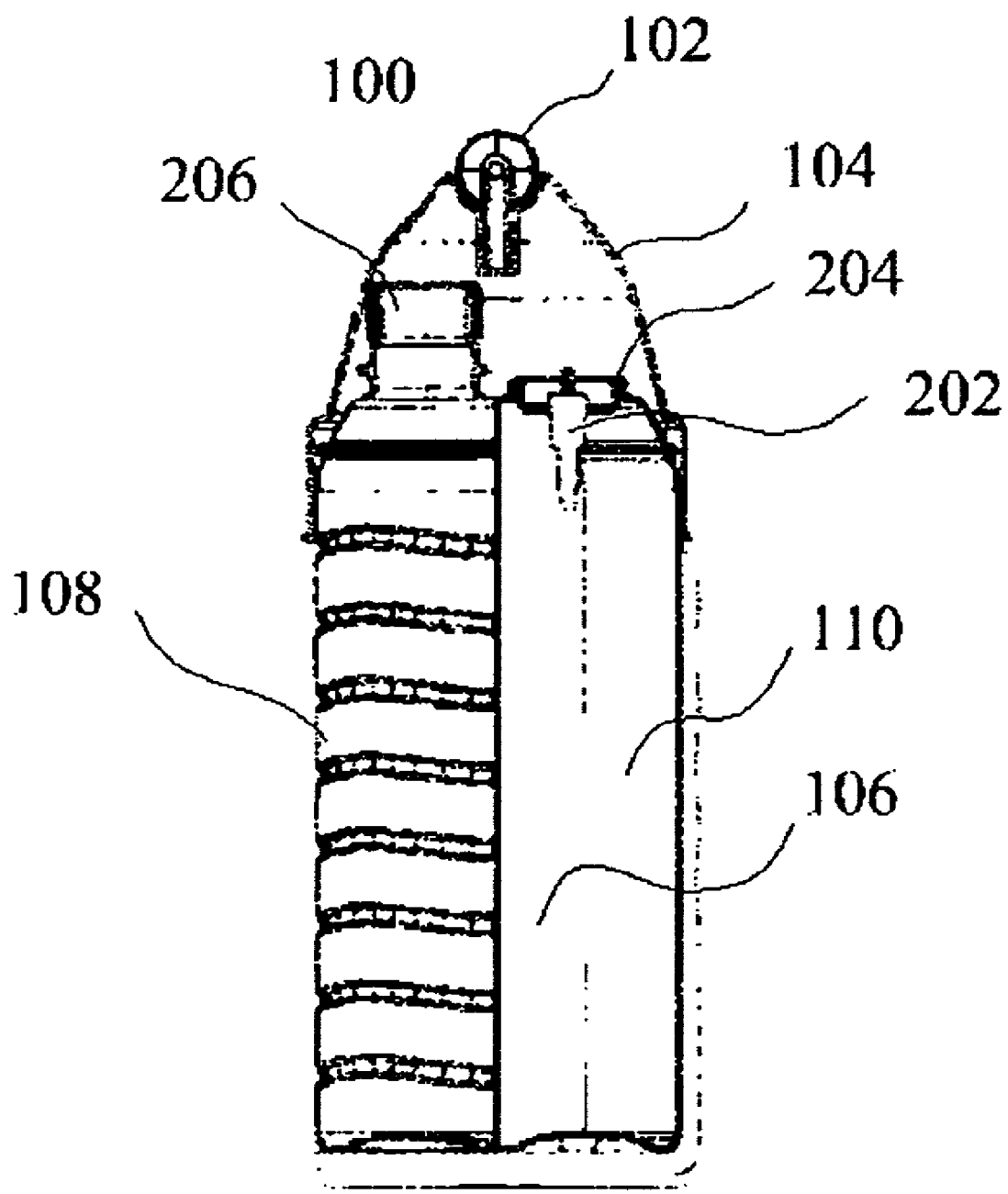
FIG. 2 shows a partial sectional view of an embodiment of the invention.
Figure 5:
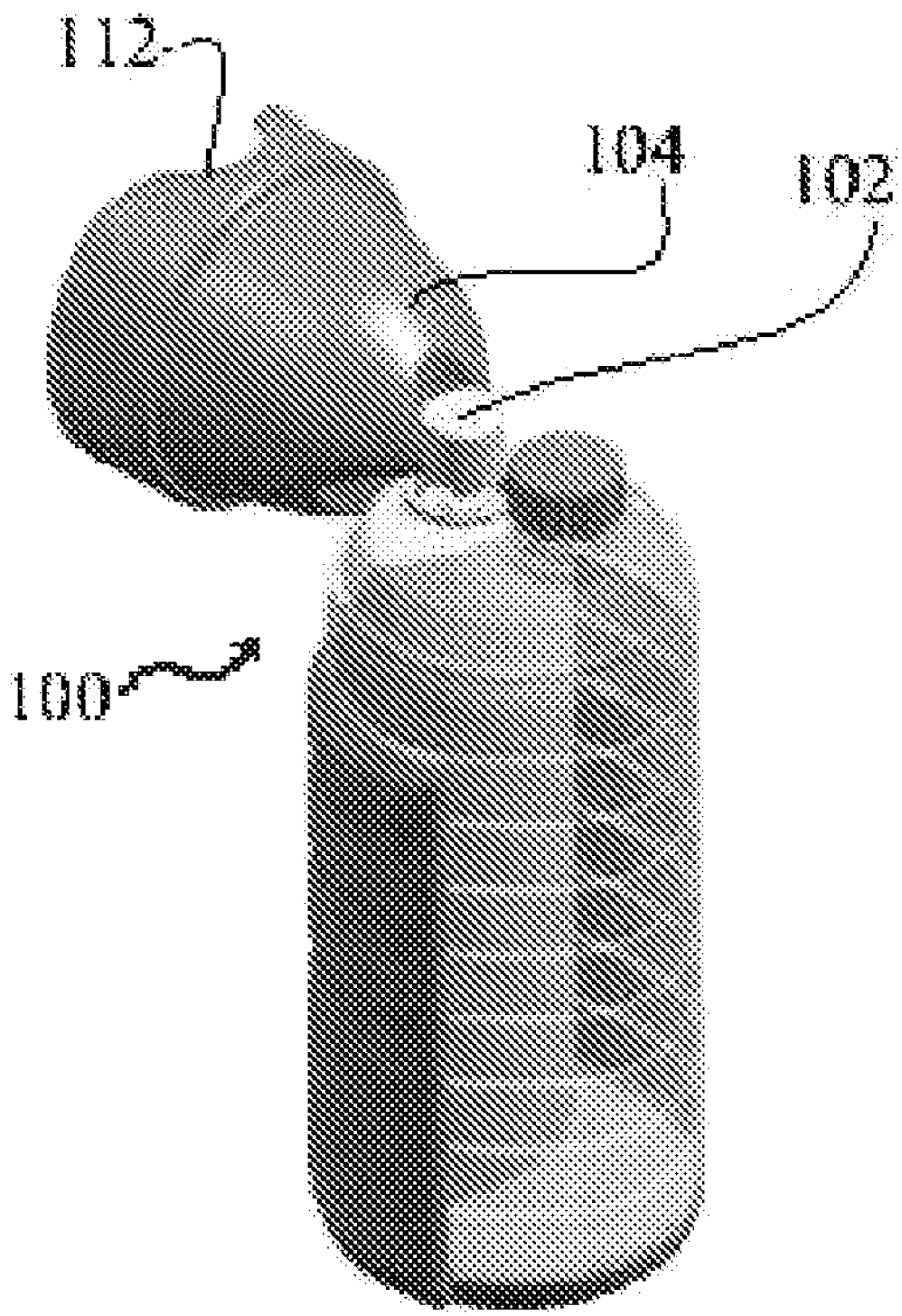
FIG. 5 is a perspective view depicting a feature of the present invention.

Referring to FIGS. 1, 2 and 5, a bottle (shown generally as 100) is shown having a valve 102 and a mask 104. The mask 104 has a cut out portion 112 that fits over a user's nose (not shown) when used to inhale oxygen. The bottle 100 consists of a water bottle 106 with an air bottle 110 partially disposed within water bottle 106 and contained within a sleeve 108. Sleeve 108 may completely surround both water bottle 106 and air bottle 110 or may only partially surround the bottles. Sleeve 108 helps hold air bottle 110 in place and gives extra structural support to bottle 100. Sleeve 108 is made of a suitable insulative material as is known in the art to provide insulative qualities to bottle 100 to help keep water cool. Mask 104 also functions as a protective cover for bottle 100 and conceals both water bottle cap 206 and oxygen nozzle 204. Oxygen nozzle 204 has a valve assembly 202 that allows oxygen to flow when valve 102 is fitted into nozzle 204 and depressed. In use, mask 104 is removed form bottle 100 and valve 102 is placed against nozzle 204. This places mask 104 in a generally horizontal orientation allowing a user to comfortably place mask 104 against face (not shown) and by pressing down on valve 102 oxygen is released allowing user to inhale oxygen. The oxygen stops flowing when valve 102 is released. Any appropriate valve structure will work as is know in the art. A biasing spring (not shown) may be used to provide a normally closed valve function. Mask 104 may be removed from nozzle 204 and used to cover bottle 100 for later use. Mask 104 may remain in place while a user removes water bottle cap 206 and drinks from the water bottle 106 or the user may temporarily remove mask 104 while drinking. Oxygen bottle 110 is ideally pressurized at a level that remains safe in the unlikely event of structural failure. Although many materials would be acceptable, PET (Polyethylene Terephthalate) Plastics are generally best for this application because PET plastics are clear, tough and are a good barrier to gas and moisture. PET plastics also have very good heat characteristics. A typical PET bottle is designed to withstand pressure of up to 150 psi. The present invention uses oxygen at a pressure well below 150 psi providing a very reliable safety margin. A typical 2 liter carbonated soft drink is pressurized at approximately 35 psi at 45 degrees F.

Figure 3:
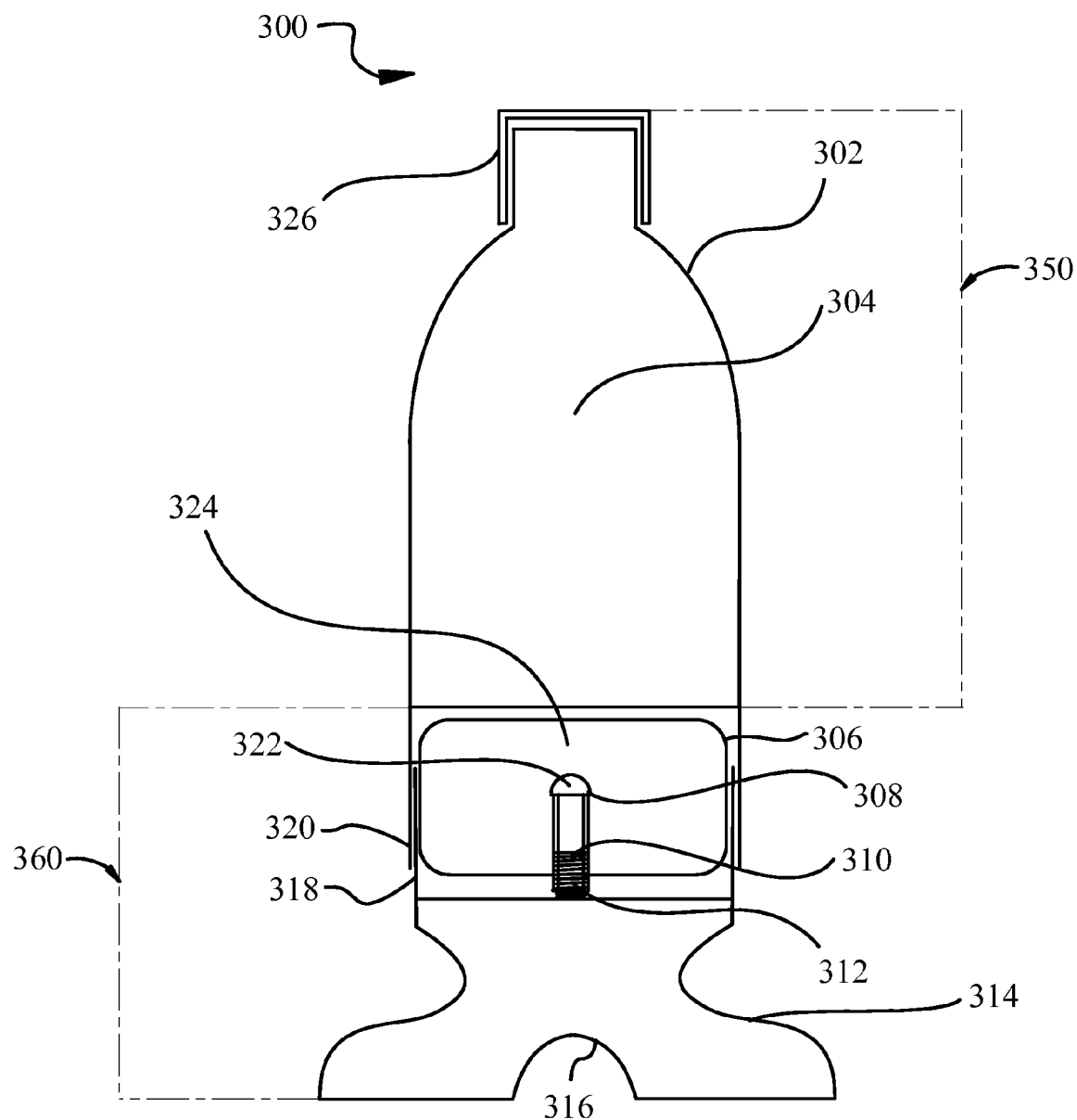
FIG. 3 shows a side view of another embodiment of the invention.

FIG. 3 illustrates another embodiment of the present invention. In this embodiment a bottle 300 also contains a water bottle 304 and an oxygen bottle 306, however the inner bottles are linearly arranged in a vertical orientation. In this embodiment, oxygen breathing mask 314 forms a natural base for bottle 300. An upper portion 350 of bottle 300 is a water bottle 302 which holds water 304 for drinking. Water 304 may be purified, spring, fortified with trace minerals, distilled, etc. as is common in the art. In other embodiments, other liquids such as soda, tea, milk or other liquid beverages may be contained by upper portion 350. A lower portion 360 of bottle 300 contains an oxygen bottle 306 which contains pressurized oxygen 324 suitable for breathing. Water bottle 302 has a conventional cap 326 used to access water 304. Again, PET plastic is used in this embodiment. A sleeve 320 extends below upper portion 350 of bottle 300 and forms a hollow space which holds oxygen bottle 306. Mask portion 314 has a corresponding sleeve 318 that press fits into upper sleeve 320 to provide a friction fit while allowing movement between the two sleeves.

Like the previous embodiment, mask 314 has a nose cutout portion 316 that allows a user to comfortably press mask 314 against the face (not shown) and breath in oxygen. Mask 314 is connected to oxygen bottle 306 by a valve 310. Valve 310 includes a central portion 322 that is connected to mask 314. A spring 31 2 biases center portion to close against a seal 308 such as an O-ring or other sealing means as is known in the art. In use, a user ensures that cap 326 is secure and turns bottle 300 over and presses mask 314 gently allowing oxygen 324 to enter mask 314. As the user stops pressing mask 314 against water bottle 302, oxygen 324 stops flowing and the user is free to drink conventionally from bottle 300.

In another embodiment, mask 314 includes a hinged sanitary cover (not shown) that covers a bottom section of mask 314 so that foreign matter will not contaminate mask 314 when bottle 300 is set down on an unclean surface. In use, a user would simply flip open the hinged cover (not shown) when breathing oxygen and then close it before setting it back down on a surface. Mask 314 may be made of any suitable material such as rubber or flexible plastic.

Figure 4:
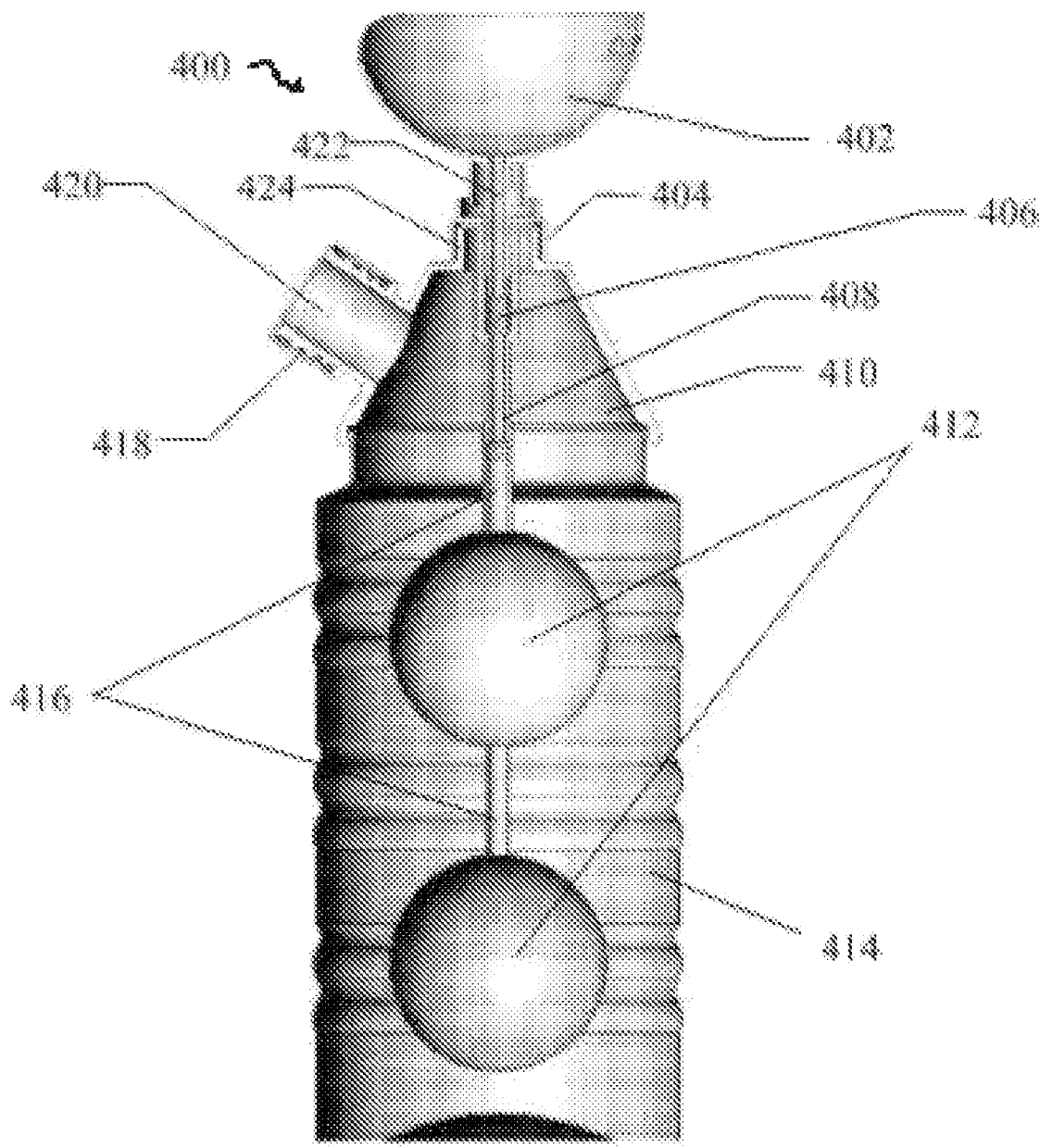
FIG. 4 is a perspective sectional view of an embodiment of the invention.

Referring now to FIG. 4, a bottle 400 is shown having two oxygen spheres 412 centrally disposed within a water bottle 414. Oxygen spheres 412 are made from any suitable material but again PET plastic is particularly well suited for this application. Although two spheres 412 are shown, other embodiments such as one, three spheres or even a radial arrangement of cylindrical oxygen cells (not shown) would be possible. Bottle 400 has a mask 402 for breathing oxygen. A user places mouth and nose against mask 402 and presses to start the flow of oxygen. The oxygen is controlled using a valve 422 that is biased with a spring 406. A stepped plunger 408 is provided to control the oxygen flow as it enters mask 402. Any suitable valve structure such as a needle valve or ball valve as is well known in the art could be used to control the flow of oxygen. Valve 422 is enclosed by a PET plastic cone 410 and includes threads 424 which fit into threaded cap 404. Water bottle 414 includes a water outlet 420 secured with a threaded cap 418.

Although the instant invention has been described in relation to particular embodiments thereof, many other variations and modifications and other uses will become apparent to those skilled in the art.

What is claimed is:

1. A hand-held container for storing a liquid and a gas comprising:
   at least one gas storage chamber generally disposed within a liquid storage bottle;
   a face mask disposed along a bottom surface of said at least one gas storage chamber with a inner surface wherein a user places mouth and nose therein;
   a connecting tube connecting said at least one gas storage chamber to said inner surface of said face mask;
   a valve disposed between said inner surface of said face mask and said at least one gas storage chamber wherein the flow of said gas is regulated;
   an outlet disposed on an outer surface of said liquid storage bottle; and
   a cap removeably connected to said outlet wherein liquid stored within said liquid storage bottle cannot leak out.

2. A container for storing a liquid and a gas according to claim 1, wherein said liquid is water.

3. A container for storing a liquid and a gas according to claim 1, wherein said gas is oxygen.

4. A water and oxygen bottle comprising:
   at least one oxygen storage chamber generally disposed within a hand held water storage bottle;
   a face mask disposed along a bottom surface of said at least one oxygen storage chamber with a inner surface wherein a user places mouth and nose therein;
   a connecting tube connecting said at least one oxygen storage chamber to said inner surface of said face mask;
   a valve disposed between said inner surface of said face mask and said at least one oxygen storage chamber wherein the flow of oxygen is regulated;
   an outlet disposed on an outer surface of said water storage bottle; and
   a cap removeably connected to said outlet wherein water stored within said water storage bottle cannot leak out.

5. A water and oxygen bottle according to claim 4, wherein said face mask is made from a flexible plastic.

6. A water and oxygen bottle according to claim 4, wherein said valve is normally closed.

7. A water and oxygen bottle according to claim 6, wherein said inner surface of said face mask is moveably connected to said valve.

8. A water and oxygen bottle according to claim 4, wherein said cap is a screw cap.

9. A water and oxygen bottle according to claim 4, wherein said face mask is removable.

10. A water and oxygen bottle according to claim 4, wherein said face mask is contoured to fit over the face and mouth of said user.

11. A water and oxygen bottle comprising:
    at least one oxygen storage chamber generally disposed within a hand held water storage bottle;
    said at least one oxygen storage chamber having a connecting surface disposed on an exterior surface therein and a bottom surface;
    a removable face mask with a inner surface disposed along said bottom surface;
    said removable face mask having a valve mounted on said inner surface wherein when said valve is placed against said connecting surface and pressed towards said connecting surface, oxygen is allowed to flow from said at least one oxygen storage chamber to said face mask;
    an outlet disposed on an outer surface of said hand held water storage bottle; and
    a cap removeably connected to said outlet wherein water stored within said hand held water storage bottle cannot leak out.

12. A water and oxygen bottle according to claim 11, wherein said removable facemask is made from rubber.

* * * * *